United States Patent [19]

Daniel et al.

[11] Patent Number: 6,011,889
[45] Date of Patent: Jan. 4, 2000

[54] PIERCING POINT OPTICAL FIBER DEVICE FOR LASER SURGERY PROCEDURES

[75] Inventors: Steven A. Daniel, Fremont; Timothy C. Reynolds, Mountain View; Zachary E. Owyang, Fremont, all of Calif.

[73] Assignee: Eclipse Surgical Technologies, Inc., Sunnyvale, Calif.

[21] Appl. No.: 08/995,963

[22] Filed: Dec. 22, 1997

Related U.S. Application Data

[63] Continuation-in-part of application No. 08/638,677, Apr. 29, 1996, Pat. No. 5,703,985.

[51] Int. Cl.[7] .............................. G02B 6/06; A61B 17/36
[52] U.S. Cl. ..................... 385/117; 385/115; 385/116; 385/38; 385/80; 606/13; 606/14; 606/15; 606/7; 606/2; 606/16; 607/1
[58] Field of Search ................................ 385/115, 116, 385/117, 119, 43, 902, 38, 76, 77, 80; 606/13, 14, 15, 16, 7, 2; 607/17, 18, 1

[56] References Cited

U.S. PATENT DOCUMENTS

| | | | |
|---|---|---|---|
| 3,556,085 | 1/1971 | Takahashi | 385/117 X |
| 4,754,328 | 6/1988 | Barath et al. | 385/117 X |
| 5,354,294 | 10/1994 | Chou | 606/16 |
| 5,459,605 | 10/1995 | Kempf | 385/117 X |
| 5,469,524 | 11/1995 | Esch et al. | 385/117 X |
| 5,498,260 | 3/1996 | Rink et al. | 606/16 |
| 5,703,985 | 12/1997 | Owyang | 385/117 |
| 5,713,894 | 2/1998 | Murphy-Chutorian et al. | 606/15 |

FOREIGN PATENT DOCUMENTS

| WO 92/10142 A1 | 6/1992 | WIPO | 385/117 X |
|---|---|---|---|

*Primary Examiner*—Brian Healy
*Attorney, Agent, or Firm*—Christopher N. Sears; Ilene L. Janofsky

[57] ABSTRACT

A device for use in laser surgical procedures for moving axially an optical fiber element that is connected at its proximal end to a source of laser energy. The distal end of the fiber elements with a cooperating piercing tip member has a tapered configuration so that it is capable of penetrating soft tissue of membrane such as the myocardium or epicardium of a human heart during the revascularization procedure. Various combinations of bundled optical fiber elements are disclosed which provide different tapered distal end designs that can be used in various surgical procedures.

21 Claims, 5 Drawing Sheets

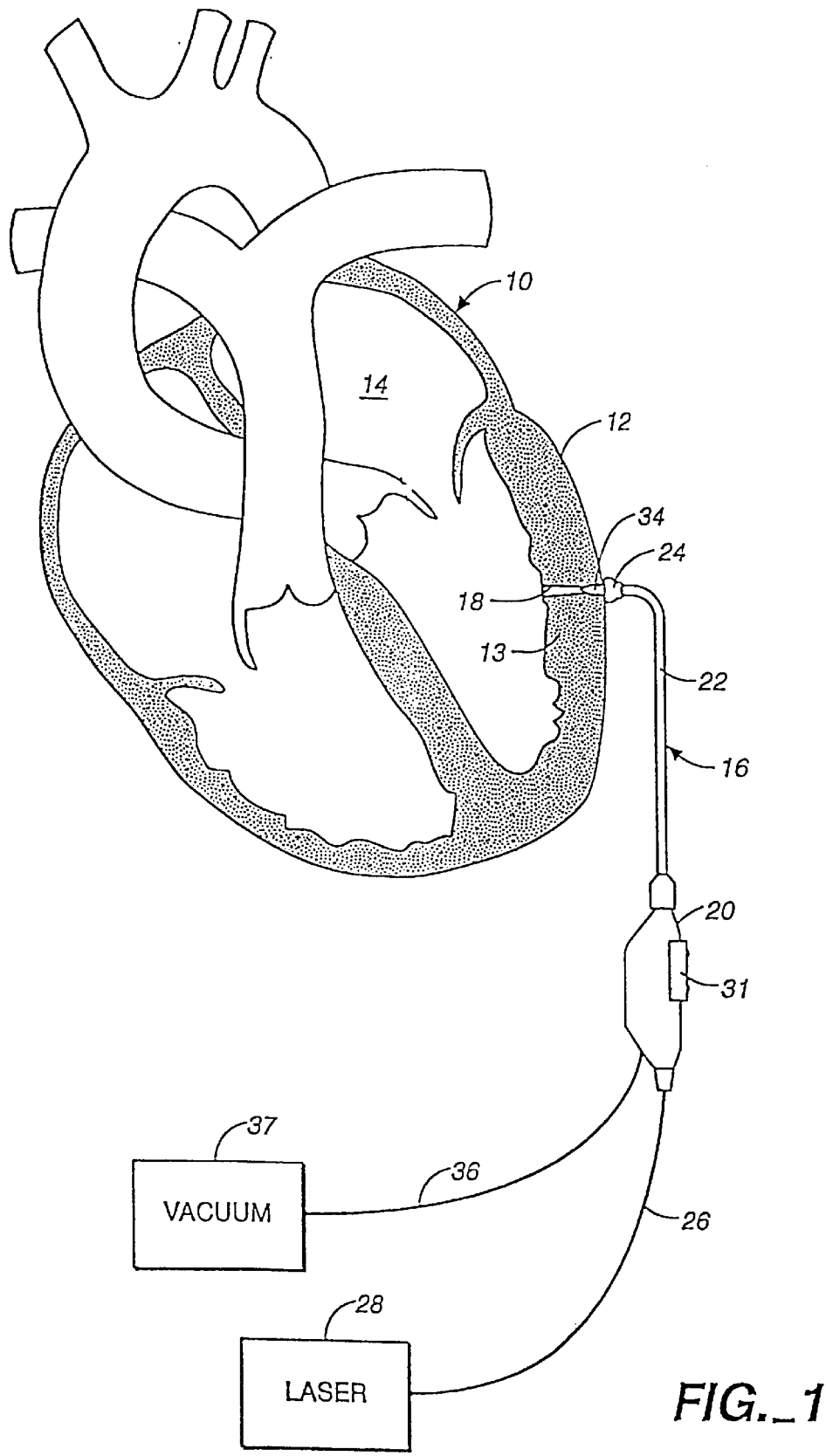
FIG._1

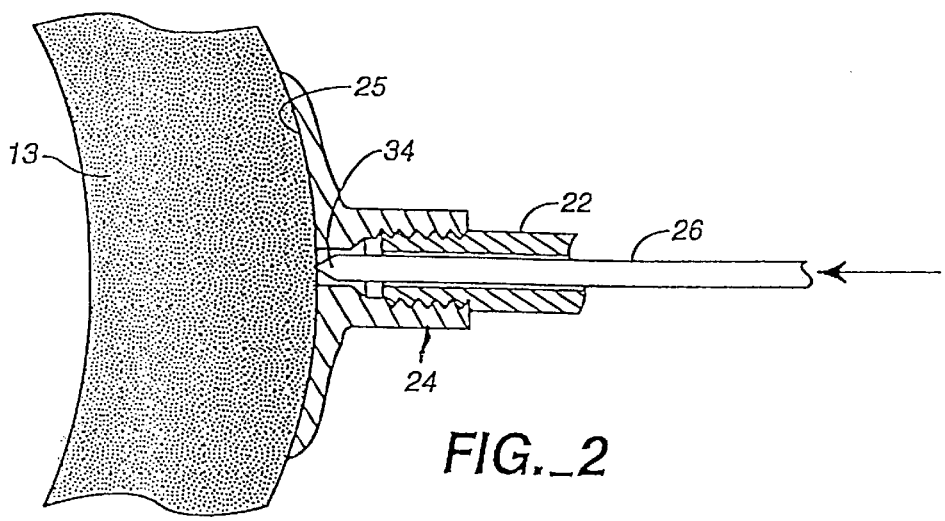
FIG._2
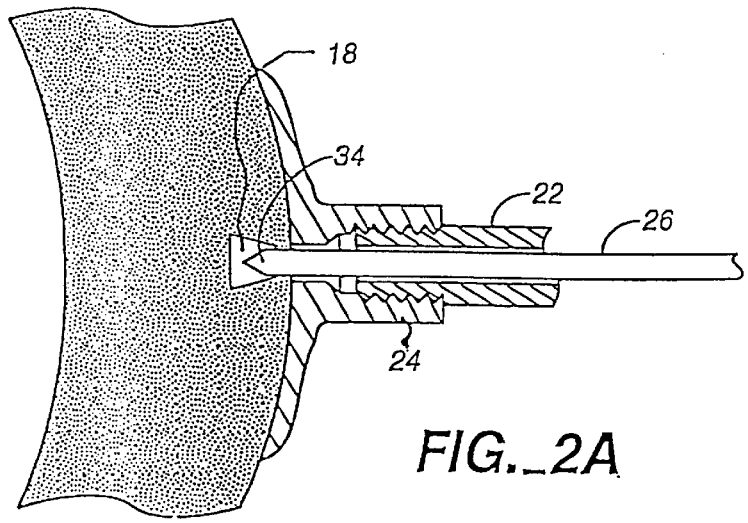
FIG._2A
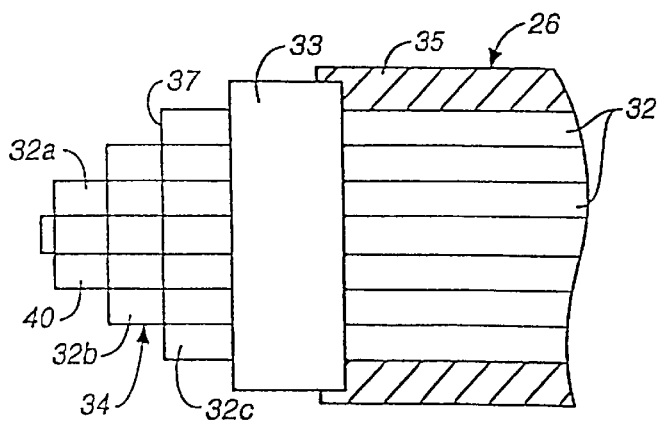
FIG._3
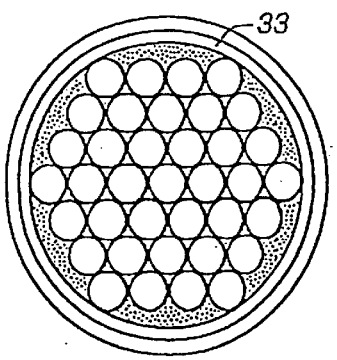
FIG._3A

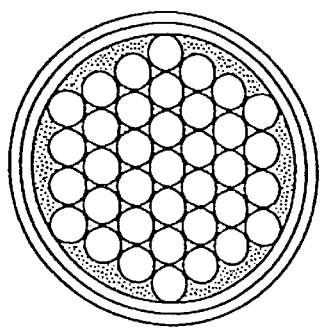
FIG._4A
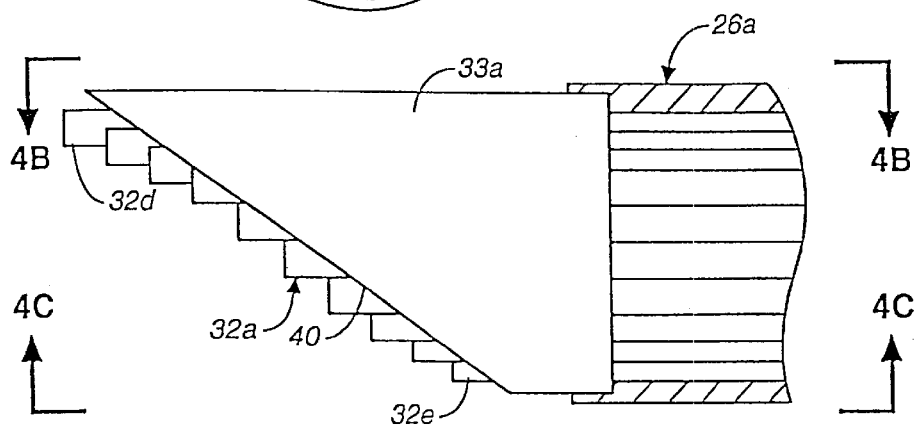
FIG._4
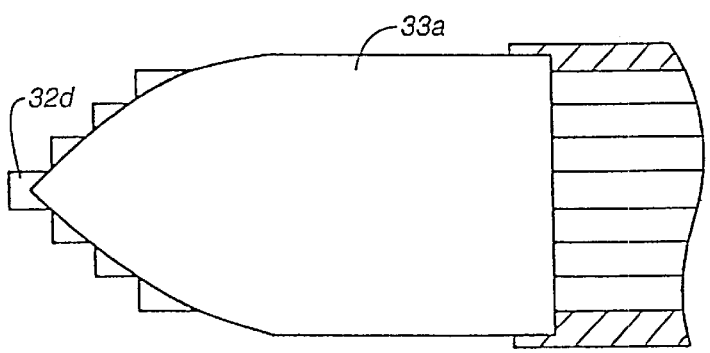
FIG._4B
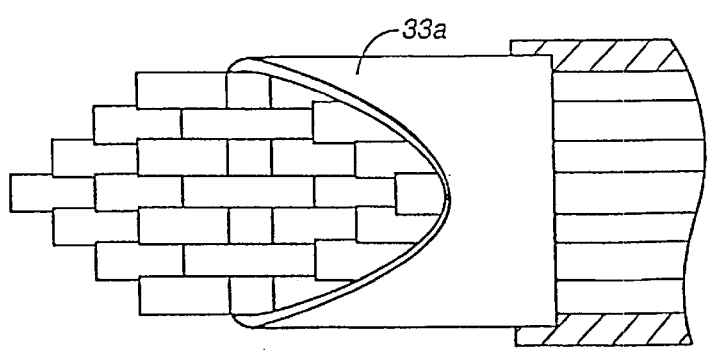
FIG._4C

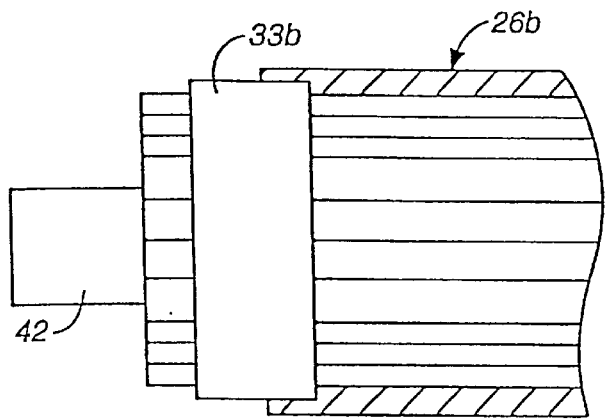
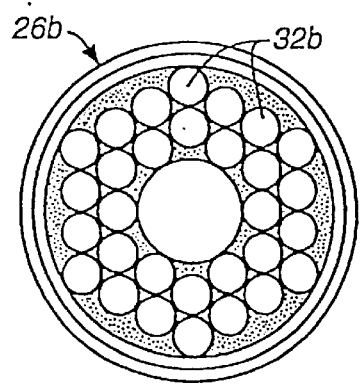
FIG._5  FIG._5A
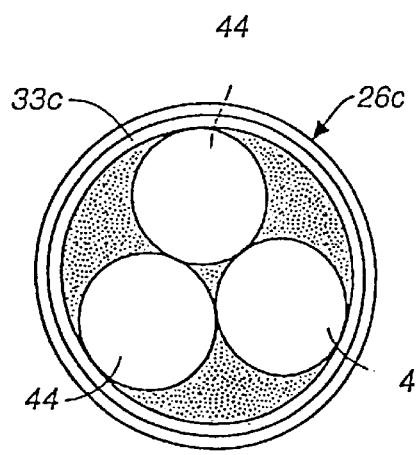
FIG._6A
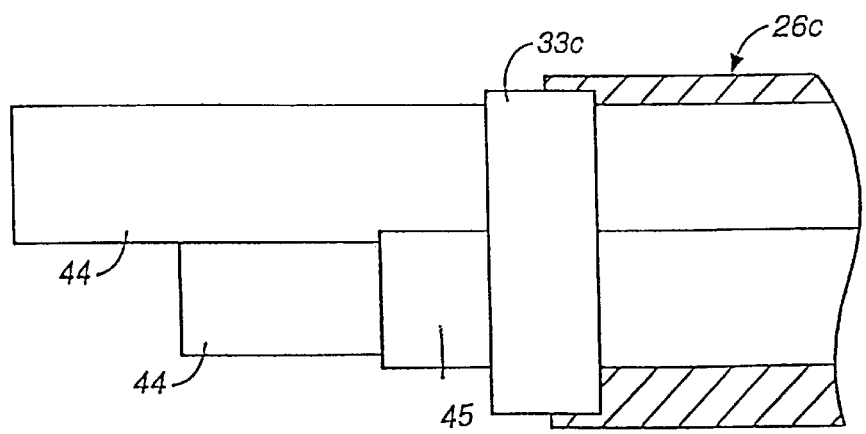
FIG._6

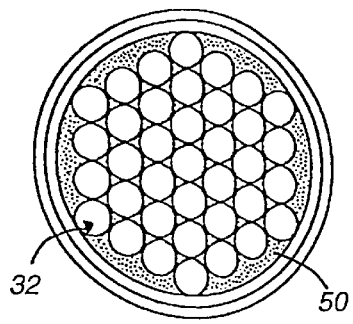
FIG._7A
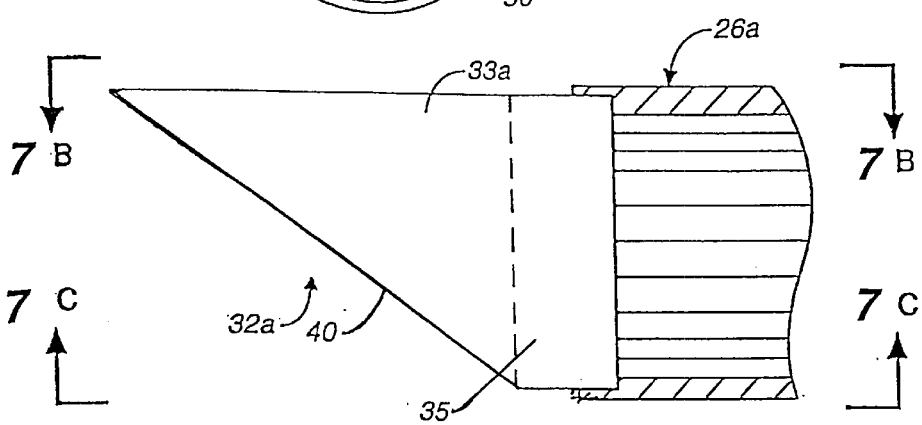
FIG._7
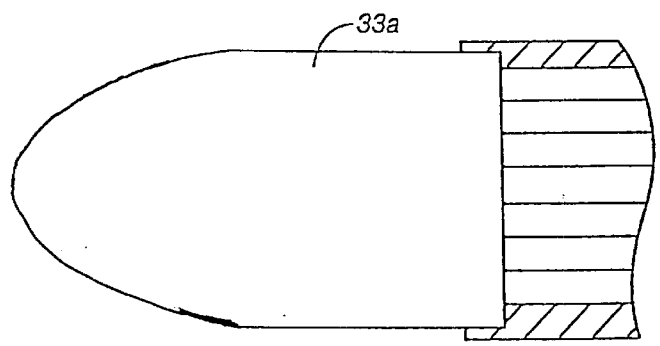
FIG._7B
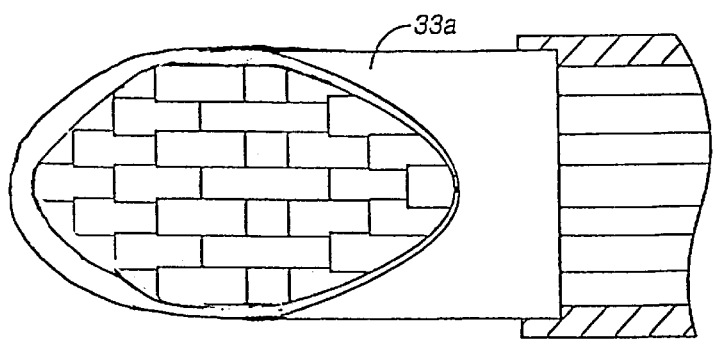
FIG._7C

PIERCING POINT OPTICAL FIBER DEVICE FOR LASER SURGERY PROCEDURES

RELATED APPLICATIONS

This application is a continuation-in-part (CIP) of U.S. patent application Ser. No. 08/638,677 filed Apr. 29, 1996, now U.S. Pat. No. 5,703,985, allowed.

FIELD OF INVENTION

This invention relates to laser surgery and more particularly to optical fiber elements adaptable for penetrating tissue and thereafter transmitting and emitting laser energy from the distal tip of such elements.

BACKGROUND OF THE INVENTION

Medical science has developed a wide variety of methods for counteracting the effects of cardiovascular disease including open heart and by-pass surgery. Non-surgical procedures such as percutaneous transluminal coronary angioplasty, laser angioplasty, and atherectomy have also been developed.

One alternative to the aforementioned procedures is known as myocardial revascularization which includes transmyocardial revascularization (TMR), percutaneous transluminal revascularization (PTMR) and minimally invasive surgical (MIS) revasularization procedures. In such procedures, channels are formed in the ventricle wall of the heart with a laser. These channels provide blood flow to ischemic heart muscle. A history and description of this method has been documented by Dr. M. Mirhoseini and M. Cayton on "Lasers in Cardiothoracic Surgery" in Lasers in General Surgery (Williams & Wilkins; 1989) pp. 216–233.

As described in the above disclosure, a CO2 laser was used to produce channels in the ventricle from the epicardium through the myocardium. This procedure followed a surgical incision in the chest wall to expose the heart. Laser energy was transmitted from the laser directly to the epicardium by means of an articulated arm device of the type commonly used for CO2 laser surgery. The beam was coherent and traveled as a collimated beam of laser energy through the epicardium, the myocardium and the endocardium into the left ventricle cavity. The epicardium received the highest energy density and therefore normally had the largest area of heart tissue removed compared with the endocardium which was approximately 1 cm deep to the epicardium. A problem associated with the above procedure arose because laser perforation of the epicardium caused bleeding from the perforation outwardly from the left ventricle after the procedure. External pressure by the surgeon's hand on the epicardium of the heart was often needed to stop bleeding from the ventricle to the outside through the hole produced by the laser in the epicardium. However, this procedure was usually only partially successful because it resulted in a significant amount of blood loss and/or an excessive amount of time required to stop the bleeding. Both factors could jeopardize the success of the revascularization procedure.

In a proposed improvement in an TMR procedure described in Hardy U.S. Pat. No. 4,658,817, a needle was added to the distal tip of an articulated arm system, with a beam of laser energy being passed through the lumen of the needle. The metal tip of the needle of the device was used to pierce most of the myocardium and the laser beam then was used to create the desired channel through the remaining portion of the myocardium and through the adjacent endocardium. In the Hardy procedure, the hollow needle used to deliver laser light was subject to being clogged by tissue or blood which could flow into the needle, thus blocking the laser light from impinging the myocardium. Also, the metal rim of the needle could be damaged by the intense laser light and leave contaminating metal remains within the myocardium which are potentially hazardous.

Another proposed TMR procedure is described in the Aita, et al. U.S. Pat. No. 5,380,316. Aita, commenting on the Hardy needle device, contended that mechanical piercing was undesirable because it entailed some degree of tearing of the pierced tissue, and that tearing often leads to fibrosis as the mechanical tear heals, a factor that severely diminishes the effectiveness of the TMR treatment. Aita, et al also contended that exposure to metal may cause fibrosis where the needle passes through tissue. The Aita, et al patent describes an elongated flexible lasing apparatus which is guided to an area exterior to the patient's heart and irradiates the exterior surface to form a channel through the epicardium, myocardium and endocardium. Thus, in the Aita et al procedure, the epicardium is irradiated at a high energy density and therefore should have a large area of heart tissue removed. Consequently, the Aita, et al procedure has the same problems and disadvantages as the prior Mirhoseini TMR procedure with respect to the aforementioned bleeding problem in the outer surface of the epicardium.

In U.S. patent application Ser. No. 08/607,782, filed Feb. 27, 1996, now U.S. Pat. No. 5,713,894, allowed, which is assigned to the assignee of the present application, an improved apparatus and method for TMR procedures is disclosed. In this application, the epicardium of the heart muscle is first penetrated mechanically by a hollow piecing member and thereafter the distal end of a laser transmitting fiber is moved forwardly through the myocardium as it emits pulses of laser energy to form a channel. When the fiber element is retracted and the piercing member is removed, the opening that was made tends to close.

Under certain operating conditions, the characteristics of the epicardium may vary so the physician may elect to use an alternative piercing means for carrying out the aforesaid improved revascularization procedure. In all cases, it is desirable that the physician be able to pierce either the endocardium or the epicardium in the most efficient manner and thereby minimize the size of the opening necessary to accommodate the advancing fiber element which the invention herein resolves.

It is therefore a general object of the present invention to provide an improved apparatus for performing laser myocardial revascularization that solves the problems of the aforementioned devices and procedures.

A further object of the present invention is to provide an optical fiber device for use in laser surgery procedures having a distal end that is configured to penetrate tissue with minimal axial force and also capable of emitting laser energy for ablating or stimulating tissue.

Another object of the invention is to provide an optical fiber device for laser surgery that has a tapered distal tip comprised of a plurality of bundled fiber members.

Yet another object of the invention is to provide an optical fiber device for laser surgery that has a tapered distal tip with at least one facet comprised of a plurality of bundled fiber members with an encasing piercing member that encloses the extremity defined by the individual optical fiber's profile.

BRIEF SUMMARY OF THE INVENTION

In accordance with the principles of the present invention a fiber optic laser catheter is provided which has a distal tip with a tapered configuration that enables it to penetrate tissue with only a small amount of axial force which the surgeon uses. In either a PTMR. MIS-TMR or a TMR procedure, a plurality of channels are created in the myocardium tissue of a major heart chamber, e.g. the left ventricle. Each channel is formed by ablating myocardium tissue with laser energy from the distal end of a fiber optic laser catheter. To minimize bleeding from outside the heart in a TMR procedure, it is preferable to first mechanically pierce the outer epicardium before laser energy is emitted as the optical fiber is moved forward. In PTMR procedure, it is desirable to first pierce the endocardium prior to ablating tissue to minimize operative effects to the endocardium.

In accordance with the present invention, the fiber optic laser catheter is comprised of a plurality of single optical fibers that are arranged in parallel and bonded together in a bundle. At the distal end of the fiber bundle, each optical fiber has a polished end face which is perpendicular to its longitudinal axis. Also, at the distal end certain individual fibers have different lengths so that the distal end of the bundle itself has a tapered configuration. The individual fibers are held firmly together by a bonding compound and are reinforced by a band of metal or plastic material that extends around the fiber bundle.

In use, the tapered distal end of the fiber bundle/piercing member is sharp enough to penetrate tissue when moved forwardly with even a small axial force. For example, in a TMR procedure, the tapered end of a fiber optic catheter with piercing member according to the invention, can be used by the surgeon to pierce the epicardium and move into the adjacent myocardium before commencing to emit laser energy from the same tapered distal tip. As the fiber optic catheter is moved forward, the emitted laser energy ablates the myocardial tissue to form a revascularization channel. When the catheter is withdrawn, the pierced hole in the epicardium which is much smaller than the ablated channel formed in the myocardium, tends to close to prevent any significant bleeding external to the heart. The fiber optic catheter with its tapered distal piercing member tip is also adaptable for use with other laser surgery procedures where initial piercing or penetration into tissue is required before laser energy is emitted from the distal tip. Another design of the present invention's optical fiber element is a distal piercing tip with at least one facet comprised of bundled optical fibers which are encased in the piercing tip whose extremity is defined by the profile of the bundled fibers.

Other objects, advantages and features of the invention will become apparent from the following detailed description of embodiments taken with the accompanying drawing.

BRIEF DESCRIPTION OF THE DRAWING

FIG. 1 is a diagrammatic view showing a typical transmyocardial revascularization procedure on a heart utilizing principles of the present invention.

FIG. 2 is an enlarged view in section showing the distal end of a device for mechanically piercing the epicardium of the heart with an optical fiber bundle.

FIG. 2A is an enlarged view in section similar to FIG. 2 showing the optical fiber bundle after its tip has pierced the epicardium.

FIG. 3 is a further enlarged view in elevation showing the tapered distal end of a fiber optic bundle according to the invention.

FIG. 3A is an end view of the fiber optic bundle shown in FIG. 3.

FIG. 4 is an enlarged view in elevation showing an alternate form of a tapered distal end of a fiber optic bundle.

FIG. 4A is an end view of the fiber optic bundle of FIG. 4.

FIG. 4B is a tip view taken along line 4B—4B of the fiber optic bundle of FIG. 4.

FIG. 4C is a bottom view of the fiber optic bundle of FIG. 4.

FIG. 5 is a fragmentary view in elevation of another alternate form of a fiber optic bundle with a tapered distal end.

FIG. 5A is an end view of the fiber optic bundle shown in FIG. 5.

FIG. 6 is a fragmentary elevation view of the distal end of another fiber optic bundle embodying principles of the invention.

FIG. 6A is an end view of the fiber bundle shown in FIG. 6.

FIG. 7 is an enlarged view in elevation showing an alternate form of a tapered distal end of a fiber optic bundle that encloses the extremity defined by a profile of the bundled fibers.

FIG. 7A is an end view of the fiber optic bundle of FIG. 7.

FIG. 7B is a tip view taken along line 7B—7B of the fiber optic bundle of FIG. 7.

FIG. 7C is a bottom view of the fiber optic bundle of FIG. 7.

DETAILED DESCRIPTION OF EMBODIMENT

FIG. 1 diagrammatically depicts a human heart 10 with the epicardium 12 of the left ventricle 14 exposed where a myocardial revascularization procedure according to the invention can be performed. This procedure initially requires making an incision in the patient's chest to expose the outer septum of the epicardium at the heart's left ventricle. In a human heart, the wall of the left ventricle comprises an outer epicardial layer 12, the myocardium 13 which is the mid-layer muscle, and the inner endocardial layer. The epicardium is a smooth, moist serous membrane that is relatively tougher than the other aforementioned tissue layers of the heart. Alternatively, the procedure can be accomplished using interventional procedural methods using a percutaneous catheter device that is positioned near the heart's endocardium for PTMR treatment. This catheter device includes an optical fiber element as similarly taught in U.S. patent application Ser. No. 08/833,352 entitled "Steerable Catheter" filed Apr. 3, 1997 issued Mar. 2, 1999 as U.S. Pat. No. 5,876,373 which can use the instant applications piercing optical fiber device. Alternatively, the instant invention could be incorporated in a minimally invasive revascularization surgical instrument as similarly taught in U.S. patent application Ser. No. 08/794,733, pending, entitled "Minimally Invasive Method For Forming Revascularization Channels".

In a TMR procedure, the surgeon uses a hand-held device 16 which is manipulated and operated to form a series of revascularization channels 18 in the myocardium of the patient's heart at selected spaced apart locations. Each of the channels 18 is formed by first piercing the epicardium to form a relatively small opening using the tapered distal end 34 of an optical fiber bundle 26 that can be moved with axial force by means of a movable control member 31 on the device 16 operated by the surgeon. The optical fiber or fiber bundle is connected to a laser energy source 28 at its proximal end. Once through the epicardial opening, laser energy is emitted from the fiber bundle as it is moved forwardly to form the channel in the myocardium and completely through the endocardium. After the channel has been formed, the distal end of the fiber or fiber bundle is retracted to a position within an enlarged end member 24 of the device 16 which can then be moved to another location to repeat the procedure. When the distal end 34 of the fiber or fiber bundle is removed, the relatively small opening in the epicardium substantially closes due to the tissue resiliency, thereby minimizing any blood flow from the formed channel.

As disclosed hereafter, the device may be connected by a flexible line 36 to a vacuum source 37 which helps to remove debris caused by laser action during a channel forming procedure and also to initiate blood flow into each channel as it is formed in order to maximize the revascularization process. It will be recognized by those skilled in the art that the device may be used with or without the vacuum source for providing suction.

Also shown in FIG. 1, the device 16 comprises a housing 20 adapted to be hand held by the surgeon during an operative procedure, a neck member 22 attached to the housing and an enlarged interchangeable distal head member 24 having a central opening. An optical fiber bundle 26 whose proximal end is connected to the laser source 28 extends through the housing, through the neck member, and through the central opening in the distal end member 24. Within the housing 20 the fiber bundle 26 is connected to a movable shuttle (not shown) that extends outside the housing and is connected to a control member 31. Thus, movement of the control member 31 by the surgeon will move the distal end 34 of the fiber bundle beyond the distal head member 24 of the neck member. The vacuum line 36 extending from the vacuum source 37 such as a conventional hospital vacuum type canister device is connected to the housing 20. Within the housing the vacuum line communicates with an air passage around the fiber bundle that extends through the neck member 22 to the distal head member 24. Thus, when in use, a suction is provided at the distal head member 24 of the device 16 which performs two vital functions. The suction force as shown in FIG. 2 draws the epicardium tissue firmly against a contacting face 25 of the distal head member 24 so that a relatively small opening can be made in the epicardium muscle fibers by the distal end of the fiber bundle 26 to enable it to penetrate further and engage the myocardium before emitting laser energy. As the fiber or fiber bundle is advanced by the surgeon beyond the epicardial opening and into the myocardium 13, laser pulses are produced from its distal end 34 to form a channel 18 through the myocardium. As the fiber or fiber bundle continues to advance, the air suction provided helps to remove debris caused by the laser and also draws blood into the channel to assure that the revascularization process will commence properly. When the fiber or fiber bundle is retracted after forming a channel, the distal end member 24 is moved away and the opening in the epicardium closes naturally with a minimum of bleeding.

Any suitable means for advancing the fiber bundle with a controlled force sufficient to penetrate through the epicardium can be used. The device 16, as shown in FIG. 1, which is particularly adapted for this purpose is described in detail in the aforementioned U.S. patent application Ser. No. 08/607,782, now U.S. Pat. No. 5,713,894, allowed, which is hereby incorporated by reference.

The proximal end of the optical fiber or optical fiber bundle 26 is connected to the source or generator 28 of laser energy which is preferably a Holmium laser that operates at a wave length in the range of 1.8 to 2.2 microns and a pulse frequency in the range of 2–25 Hertz. This type of laser is preferable because it provides high absorption efficiency, hemostosis and a moderate absorption range in the myocardium, and is compatible with optical fiber delivery.

At the laser generator, laser energy is supplied to the optical fiber or optical fiber bundle 26 which, at its distal end, has a diameter of around 1 mm. In one typical form, shown in FIGS. 3 and 3A, the optical fiber bundle 26 is comprised of a plurality (e.g. 37) of individual glass fibers 32 each having a diameter of 100 microns. These glass fibers are held together by a suitable bonding material, such a 353 ND Epoxy, and near its distal tip, the bundle is preferably surrounded by an annular tantalum marker 33 which serves to retain the bundle in a closely packed geometric boundary. Surrounding the bundled fibers is a plastic protective sheath 35 having a wall thickness of approximately 0.004 inches. The sheath may be made of a metal material or plastic, such as polypropylene. The sheath further may be formed as a coil spring.

In accordance with the present invention, the tip of each optical fiber is polished to form an end face 37 that is perpendicular to its longitudinal axis so that a beam of laser energy is emitted axially from each fiber end face and the energy from adjacent fibers merge into a single beam. An important feature of the invention is that the tips of the optical fibers of the fiber bundle are spaced apart longitudinally so that the distal tip of the fiber bundle can generally be of a tapered configuration. This enables the fiber bundle to pierce the epicardium to form an opening therein so that it can then be moved forward into the myocardial tissue before emitting laser energy to ablate tissue and form a channel 18.

In the embodiment of FIG. 3, a bundle 26 of optical fibers 32 has a tapered distal tip 34 that is formed by a cluster 40 of seven fibers 32(a) around the central axis of the bundle that are the longest of the bundle and extend a fixed predetermined distance, e.g. 0.025 mm beyond an adjacent intermediate ring of 12 fibers 32(b) which in turn extend the same distance, e.g. 0.025 mm beyond an outer ring of 18 fibers (32c). The aforesaid arrangement provides a distal end for a fiber bundle 26 which can emit a uniform beam of laser energy and yet has a structural configuration that will enable it to pierce and penetrate the epicardium with a reasonable amount of axial force.

An alternate form of a tapered distal tip 34(a) according to the invention is illustrated in FIGS. 4–4C. Here, the fiber bundle 26(a) having a pre-selected number of optical fibers (e.g. 37), is held together by epoxy material and a metal or plastic material 33(a) which also serves as a marker. The individual fibers of the bundle vary in length along a plane 40 that intersects the axis of the bundle at an angle as shown in FIG. 4.

Thus, the longest of the fibers 32(d) are at one side of the bundle and adjacent fibers are reduced progressively by a predetermined amount (e.g. 0.025 mm) toward the opposite side of the bundle where the shortest fiber 32(e) is shown. The resulting distal tip configuration of this arrangement is relatively sharp which readily enables it to penetrate the epicardium with moderate axial force.

In the embodiment of FIGS. 5 and 5A, a single central fiber 42 having a diameter of 0.02 mm at the central axis of a bundle 26(b) is surrounded by a plurality of smaller fibers that can be 30 in quantity, having a diameter of 0.01 mm. The central fiber 42 extends co-axially but approximately 0.032 mm longitudinally beyond the surrounding fibers 32(b). In this embodiment, the bundled fibers are again held together by an epoxy binder and a metallic ring marker 33(b) made of tantalum.

Another embodiment of a fiber bundle with tapered tip is shown in FIGS. 6 and 6A. Three relatively large fibers 44 and 45 having a diameter of 0.02–0.03 mm are held together in a bundle 26C by epoxy and a ring member 33(c). Beyond the ring member, the tip ends of the three fibers extend for different lengths to provide a generally tapered distal tip configuration. Thus, the longest fiber extends 0.03–0.07 mm beyond an intermediate fiber which extends 0.03–0.07 mm beyond the shortest fiber 45.

Referring now to FIGS. 7–7C, an alternate optical fiber distal piercing tip design is shown. FIG. 7 is an enlarged view in elevation showing a tapered fiber optic bundle's distal end that encloses the extremity of the optical fiber bundle's profile. Tapered distal tip 32a according to the invention shows the fiber bundle 26a having a pre-selected number of optical fibers that are held together by epoxy material 50. Preferably, a metal, plastic or an epoxy material is used to form a band member 33(a) that encloses the extremity defined by the distal end profile of the bundled fibers 26a, the band 33a can also be a radiopaque marker. The band 33a can be made from either a single material such as metal or epoxy, or a combination of materials such as an epoxy material that forms the distal tapered distal tip 32a optionally joined with a proximally located tantalum band 35. The band 33a can be made from tantalum alone. The individual optical fibers 32 vary in length along facet plane 40 that intersects the axis of the bundle at an angle as shown in FIG. 7. The band 33a minimizes breakage of the individual distal tip's of the optical fibers 32. The longest of the optical fibers are at one side of the bundle 26a and adjacent fibers are reduced progressively by a predetermined amount (e.g. 0.025 mm) toward the opposite side of the bundle where the shortest fiber is located. The resulting tapered distal tip 32a is relatively sharp thereby enabling tissue penetration through either an endocardium or an epicardium with moderate axial force, yet still is atraumatic. The optical fiber bundle 26a has at least one outer surface lying in a plane forming an oblique angle with respect to an axis of the optical fiber 32 for efficacious tissue piercing. This can typically be 30–60 degrees. Moreover, the distal tip can have multiple facets where each facet surface forms a plane at an oblique angle with respect to the optical fiber element's axis.

The fiber bundle 26a shown in FIG. 3 can be made using several methods. One method initially starts by using square-polished fibers 32 that are sequentially built-up. The mid-layer 32b is formed by using a mold and mandrel or beading of material such as tetrafluoroethylene that positions a group of optical fibers 32 in a ring, e.g. twelve 100 micron fibers. Potting material, such as thermally cured epoxy is applied and cured. The beading is subsequently removed. An outer layer uses a larger mold and mandrel or beading for a next ring of fibers to be conjoined therewith, e.g. combining nineteen more 100 micron fibers using epoxy followed by subsequent curing. The beading is removed and the mid-layer and seven hundred micron fibers are inserted into the outer layer. The distal tip is arranged in a stepped formation which forms the piercing tip. The entire assembly is potted with epoxy and cured. The marker band member 33 made tantalum can be press fitted to encase the optical fiber(s) 32.

A method for constructing the optical fiber piercing tip of FIG. 7 is to bundle the optical fibers 32 that initially are square-polished elements into a staggered configuration by pushing fibers against a mold having a requisite conformal angled face 40 of the tapered distal tip 32a. Epoxy 50 is used to pot the fibers against a mold having the angled face. Epoxy can also be used to form the distal tapered tip 40 to pot the fibers at the tip such that it encapsulates the fibers with a band that has sufficient thickness to ensure durability, i.e. typically at least the thickness of an optical fiber with a 100 microns diameter. A band member 35 such as metal, e.g. tantalum, may be bonded behind the tip to support and pack the bundle in a tightly uniform configuration and can also extend and form the piercing tip 32(a) which becomes the leading piercing edge 40. After potting material curing has occurred of the tapered tip 33a, bundle 26a can optionally be subjected to laser irradiation to burn off any excess potting materials formed on the ends of the fibers 50 during the band 33a formation to complete construction.

It will be recognized by those skilled in the art that the number and diameters of fibers bundled in the various embodiments shown and described may vary. For instance, a single optical fiber element could have a piercing tip design as taught herein. Accordingly, the angle formed at the tapered tip may vary and the distances between adjacent longer/shorter fibers also may vary. Additionally the use of potting materials around the bundled fibers also may affect the angle of taper. The surgical piercing optical fiber of the instant invention could also be used in other surgical instruments for different procedures that use laser energy delivery optical fibers for delivering laser energy to treat internal organs, for example the prostate.

In all of the aforesaid embodiments a bundle of optical fibers held tightly together are provided with a tapered distal tip configuration. When used with a suitable device such as the device 16, as shown, the tapered fiber bundle can first mechanically penetrate the epicardium during a revascularization procedure before emitting laser energy to form the revascularizing channel. Yet, when the fiber bundle is withdrawn the relatively small opening that it made in either the endocardium or the epicardium will close naturally due to tissue resiliency.

To those skilled in the art to which this invention relates, many changes in construction and widely differing embodiments and applications of the invention will make themselves known without departing from the spirit and scope of the invention. The disclosure and the description herein are purely illustrative and are not intended to be in any sense limiting.

What is claimed is:

1. A device for use in a laser surgical procedure comprising:
    at least one flexible optical fiber having a proximal end configured for connecting to a laser energy source; and
    a distal end of the at least one optical fiber is enclosed and permanently affixed to a piercing member that encompasses an extremity profile defined by the at least one optical fiber wherein the at least one optical fiber is substantially disposed within the piercing member's central region,
    whereby the device is capable of penetrating tissue for subsequent laser energy emissions within adjacent tissue.

2. The device of claim 1 wherein the at least one optical fiber is multiple optical fibers defining a fiber bundle, the optical fibers are arranged at longitudinal distances apart such that the fiber bundle's distal end is enclosed by the piercing member.

3. The device of claim 2 further including potting means for bringing the fibers together to form the fiber bundle, a band member surrounds the fiber bundle wherein the band member is the piercing member.

4. The device of claim 2 wherein the optical fibers all have tip faces which are perpendicular to a longitudinal axis of each optical fiber.

5. The device of claim 3 wherein the band member is tubular and made of tantalum.

6. The device of claim 4 wherein an optical fiber on one side of the fiber bundle is the longest fiber and a fiber on the opposite side is the shortest fiber of the fiber bundle and the intermediate fibers between the longest and shortest fibers have end faces that terminate generally along a plane that cuts diagonally at a pre-selected angle across the bundle and across the end faces of the longest and shortest fibers, whereby the device's distal end is a composite tapered structure.

7. The device of claim 6 wherein the pre-selected angle is around 60 degrees relative to the longitudinal axis of the fiber bundle.

8. The device of claim 6 wherein the end faces of adjacent fibers along the plane are spaced apart by 0.02 to 0.03 mm.

9. The device of claim 6 wherein the band member is a composite structure whose a) proximal end is an annular metallic band and b) distal end is an epoxy tapered tip structure that extends over all of the outer optical fiber members.

10. The device of claim 6 wherein the fiber bundle is comprised of three optical fibers each having a diameter of around 0.02–0.03 mm.

11. The device of claim 10 wherein the end faces of the fiber members are spaced apart a distance of 0.03–0.04 mm.

12. The device as described in claim 2 wherein the piercing member is made from a epoxy potting material that consolidates the optical fibers thereby forming and enclosing the fiber bundle, and the piercing member's distal end has a minimal wall thickness dimensionally similar as outer most optical fiber's diameter in the optical fiber bundle.

13. The device of claim 1 wherein the at least one optical fiber is a single fiber whose tip face is perpendicular to a longitudinal axis of the single optical fiber.

14. The device as described in claim 1 wherein the piercing member is a potting material on at least the extremity profile of the at least one optical fiber.

15. A device for use in a laser surgical procedure comprising:

multiple optical fibers defining an optical fiber bundle having a proximal end configured for connecting to a laser energy source; and a distal end of the optical fiber bundle is enclosed and permanently affixed to a piercing member that encompasses an extremity profile defined by the optical fiber bundle that is disposed substantially within the a central region of the piercing member wherein the optical fibers are arranged at longitudinal distances apart such that the fiber bundle's distal end is enclosed by the piercing member, whereby the device is capable of penetrating tissue for subsequent laser energy emissions within adjacent tissue.

16. The device of claim 15 further including potting means for bringing the fibers together to form the fiber bundle, a band member surrounds the fiber bundle wherein the band member is the piercing member.

17. The device of claim 15 wherein the optical fibers have tip faces which are perpendicular to a longitudinal axis of each optical fiber.

18. The device of claim 16 wherein the band member is tubular and made of tantalum.

19. The device as described in claim 15 wherein the piercing member is made from a epoxy potting material that consolidates the optical fibers thereby forming and enclosing the fiber bundle, and the piercing member's distal end has a minimal wall thickness dimensionally similar as outer most optical fiber's diameter in the optical fiber bundle.

20. The device of claim 17 wherein an optical fiber on one side of the fiber bundle is the longest fiber and a fiber on the opposite side is the shortest fiber of the fiber bundle and the intermediate fibers between the longest and shortest fibers have end faces that terminate generally along a plane that cuts diagonally at a pre-selected angle across the bundle and across the end faces of the longest.

21. A myocardial revascularization treatment device comprising:

a distal end having a bonded combination of a plurality of optical fibers configured for connection to a laser energy source having end faces essentially perpendicular to a longitudinal axis and arranged at longitudinal distances apart, and a material element formed into a piercing tip member with at least one facet, said combination having an extremity profile defined by the plurality of optical fibers.

* * * * *